United States Patent [19]
Lang et al.

[11] Patent Number: 5,866,610
[45] Date of Patent: Feb. 2, 1999

[54] SUBSTITUTED BENZOYLGUANIDINES, PROCESS FOR THEIR PREPARATION, THEIR USE AS A PHARMACEUTICAL AS INHIBITORS OF THE CELLULAR NA+/H+ EXCHANGE OR AS A DIAGNOSTIC, AND PHARMACEUTICAL CONTAINING THEM

[75] Inventors: Hans-Jochen Lang, Hofheim/Taunus; Andreas Weichert, Frankfurt am Main; Heinz-Werner Kleemann, Bad Homburg; Jan-Robert Schwark, Frankfurt am Main; Wolfgang Scholz, Eschborn; Udo Albus, Florstadt, all of Germany

[73] Assignee: Hoechst Aktiengesellschaft, Frankfurt am Main, Germany

[21] Appl. No.: 683,141

[22] Filed: Jul. 18, 1996

Related U.S. Application Data

[63] Continuation of Ser. No. 391,272, Feb. 21, 1995, abandoned, which is a continuation of Ser. No. 198,812, Feb. 18, 1994, abandoned.

[30] Foreign Application Priority Data

Feb. 20, 1993 [DE] Germany .......................... 43 05 250.9

[51] Int. Cl.⁶ ........................ A61K 31/165; C07C 233/65
[52] U.S. Cl. ........................... 514/617; 514/614; 514/615; 514/619; 514/622; 514/821; 558/415; 564/161; 564/163; 564/165; 564/166; 564/167
[58] Field of Search ..................... 564/147, 149, 564/237, 241, 161, 163, 165, 166, 167; 514/614, 615, 634, 821, 524, 617, 619, 622; 558/615

[56] References Cited

U.S. PATENT DOCUMENTS

| | | |
|---|---|---|
| 3,780,027 | 12/1973 | Cragoe, Jr. et al. .................... 564/85 |
| 4,251,545 | 2/1981 | Resnick .................................. 424/324 |
| 4,544,670 | 10/1985 | Studt et al. ............................. 514/617 |
| 5,091,394 | 2/1992 | Englert et al. ......................... 514/331 |

FOREIGN PATENT DOCUMENTS

| | | |
|---|---|---|
| 0556672A1 | 8/1993 | European Pat. Off. . |
| 0556674A1 | 8/1993 | European Pat. Off. . |
| 3502629A1 | 7/1986 | Germany . |
| 1514198 | 6/1978 | United Kingdom ............... 514/634 |

*Primary Examiner*—Shailendra Kumar
*Attorney, Agent, or Firm*—Finnegan, Henderson, Farabow, Garrett & Dunner, L.L.P.

[57] ABSTRACT

Substituted benzoylguanidines, process for their preparation, their use as a pharmaceutical or diagnostic, and pharmaceutical containing them.

Described are benzoylguanidines of the formula I

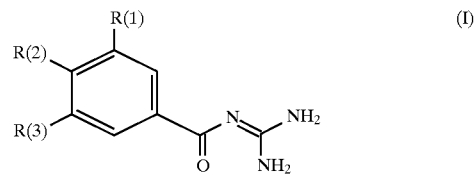

where R(1) to R(3) are H, Hal, (cyclo)alkyl, $N_3$, CN or OH, alkyloxy, phenyl, phenoxy or benzoyl, and their pharmacologically acceptable salts, but with the exception of the compounds benzoylguanidine, 4-chlorobenzoylguanidine, 3,4-dichlorobenzoylguanidine and 3- or 4-methylbenzoylguanidine.

They are obtained by reacting a compound II

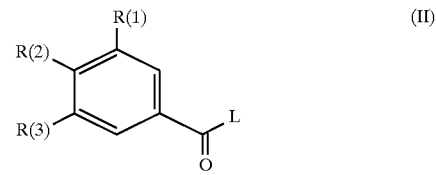

with guanidine, L being a leaving group.

6 Claims, No Drawings

SUBSTITUTED BENZOYLGUANIDINES, PROCESS FOR THEIR PREPARATION, THEIR USE AS A PHARMACEUTICAL AS INHIBITORS OF THE CELLULAR NA+/H+ EXCHANGE OR AS A DIAGNOSTIC, AND PHARMACEUTICAL CONTAINING THEM

This application is a continuation of application Ser. No. 08/391,272, filed Feb. 21, 1995 abandoned, which is a continuation of prior application Ser. No. 08/198,812, filed Feb. 18, 1994, abandoned, which application is entirely incorporated herein by reference.

The invention relates to benzoylguanidines of the formula I

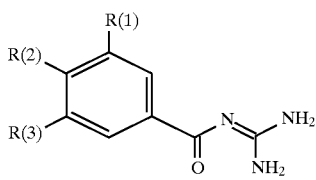

in which:

R(1), R(2), R(3) are hydrogen, F, Cl, Br, I or $(C_1-C_{12})$-alkyl, one of the substituents R(1), R(2) or R(3) is $N_3$, CN, OH or $(C_1-C_{10})$-alkyloxy, if at least one of the remaining substituents R(1), R(2) or R(3) is a sufficiently lipophilic alkyl radical having 3 to 12 carbon atoms, or one of the substituents R(1), R(2) or R(3) is R(4)— $C_nH_{2n}$—$O_m$ where
m is zero or 1,
n is zero, 1, 2 or 3,
R(4) is $C_pF_{2p+1}$
where p is 1, 2 or 3 if n is zero or 1, or
R(4) is $(C_3-C_{12})$-cycloalkyl, phenyl, pyridyl, quinolyl or isoquinolyl, the aromatic and heteroaromatic ring systems being unsubstituted or substituted by a substituent selected from the group comprising F, Cl, $CF_3$, methyl, methoxy or NR(5)R(6), where R(5) and R(6) are hydrogen or $(C_1-C_4)$-alkyl, or one of the substituents R(1), R(2) or R(3) is —C≡CR(5), —C[R(6)]=CR(5), R(5) is
phenyl which is unsubstituted or substituted by 1–3 substituents selected from the group comprising F, Cl, $CF_3$, methyl, methoxy, hydroxyl, amino, methylamino or dimethylamino,
$(C_1-C_9)$-heteroaryl, which is unsubstituted or substituted as phenyl,
$(C_1-C_6)$-alkyl, which is unsubstituted or substituted by 1–3 OH, or
$(C_3-C_8)$-cycloalkyl, R(6) is hydrogen or methyl, and the pharmacologically acceptable salts thereof, where, if R(4) is pyridyl, quinolyl or isoquinolyl, m and n must not simultaneously be zero, and with the exception of the compounds benzoylguanidine, 4-chlorobenzoylguanidine, 3,4-dichlorobenzoylguanidine, and 3- or 4-methylbenzoylguanidine.

Preferred compounds are those in which

R(1), R(2), R(3) are hydrogen, F, Cl, Br or $(C_1-C_8)$-alkyl
one of the substituents R(1), R(2) or R(3) is OH or $(C_1-C_6)$-alkyloxy, if at least one of the remaining substituents R(1), R(2) or R(3) is a sufficiently lipophilic alkyl radical having 3 to 6 carbon atoms, or one of the substituents R(1), R(2) or R(3) is R(4)— $C_nH_{2n}$—$O_m$ where
m is zero or 1,
n is zero, 1, 2 or 3,
R(4) is $C_pF_{2p+1}$
where p is 1 if n is zero or 1, or
R(4) is $(C_5-C_7)$-cycloalkyl, phenyl, pyridyl, quinolyl or isoquinolyl, the aromatic and heteroaromatic ring systems being unsubstituted or substituted by a substituent selected from the group comprising F, Cl, $CF_3$, methyl or methoxy, or one of the substituents R(1), R(2) or R(3) is —C≡CR(5),
R(5) is phenyl or $(C_1-C_4)$-alkyl,
which is unsubstituted or substituted by OH, and the pharmacologically acceptable salts thereof, where, if R(4) is pyridyl, quinolyl or isoquinolyl, m and n must not simultaneously be zero, and with the exception of the compounds benzoylguanidine, 4-chlorobenzoylguanidine, 3,4-dichlorobenzoylguanidine and 3- or 4-methylbenzoylguanidine.

Particularly preferred are 3-trifluoromethylbenzoylguanidine hydrochloride, 3,5-bistrifluoromethylbenzoylguanidine hydrochloride, 3-methyl-5-trifluoromethylbenzoylguanidine hydrochloride, 4-fluoro-3-trifluoromethylbenzoylguanidine hydrochloride, 4-(4-fluorophenoxy)-3-trifluoromethylbenzoylguanidine hydrochloride, 5-fluoro-3-trifluoromethylbenzoylguanidine hydrochloride, 3-chloro-4-isopropylbenzoylguanidine hydrochloride, 4-tert-butyl-3-methoxybenzoylguanidine hydrochloride, 3-tert-butyl-4-hydroxybenzoylguanidine hydrochloride, 3-tert-butyl-4-isopropylbenzoylguanidine hydrochloride and the pharmacologically acceptable salts thereof.

If one of the substituents R(1) to R(3) contains an symmetric centre, then the invention also embraces S- and R-configurated compounds. The compounds can be in the form of optical isomers, diastereomers, racemates or mixtures of these.

The alkyl radicals mentioned can be either straight-chain or branched.

$(C_1-C_9)$-heteroaryl is to be understood as meaning, in particular radicals which are derived from phenyl or naphthyl and in which one or more CH groups are replaced by nitrogen and/or in which at least two adjacent CH groups (on the formation of a five-membered aromatic ring) are replaced by S, NH or O. Moreover, it is also possible for one or both atoms of the condensation site of bicyclic radicals (such as in indolizinyl) to be nitrogen atoms.

Heteroaryl is, in particular, furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, cinnolinyl.

The invention furthermore relates to a process for the preparation of a compound I, which comprises reacting a compound of the formula II

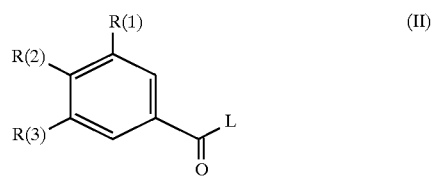

in which R(1) to R(3) have the abovementioned meaning and L is a leaving group which can readily be substituted by a nucleophile, with guanidine.

The activated acid derivatives of the formula II in which L is an alkoxy group, preferably a methoxy group, a phenoxy group, a phenylthio, methylthio or 2-pyridylthio group, or a nitrogen heterocycle, preferably 1-imidazolyl, are obtained advantageously, in a manner known per se, from the carboxylic acid chlorides on which they are based (formula II, L=Cl), which, in turn, can be prepared from the carboxylic acids on which they are based (formula II, L=OH), in a manner known per se, for example using thionyl chloride.

In addition to the carboxylic acid chlorides of the formula II (L=Cl), further activated acid derivatives of the formula II can also be prepared in a manner known per se directly from the benzoic acid derivatives on which they are based (formula II, L=OH), for example the methyl esters of the formula II where L=OCH$_3$ by treating them with gaseous HCl in methanol, the imidazolides of the formula II by treating them with carbonyldiimidazole (L=1-imidazolyl, Staab, Angew. Chem. Int. Ed. Engl. 1, 351–367 (1962)), the mixed anhydrides II using Cl—COOC$_2$H$_5$ or tosyl chloride in the presence of triethylamine in an inert solvent, and benzoic acids can be activated using dicyclohexylcarbodiimide (DCC) or using O-[(cyano(ethoxycarbonyl) methylene)amino]-1,1,3,3-tetramethyluronium tetrafluoroborate ("TOTU") [Proceedings of the 21st European Peptide Symposium, Peptides 1990, Editors E. Giralt and D. Andreeu, Escom, Ledien, 1991). A series of suitable methods for the preparation of activated carboxylic acid derivatives of the formula II is given in J. March, Advanced Organic Chemistry, Third Edition (John Wiley & Sons, 1985), p. 350, where the references are cited.

An activated carboxylic acid derivative of the formula I is reacted with guanidine in a manner known per se, in a protic or aprotic polar, but inert, organic solvent. Substances which have proven themselves in the reaction of the methyl benzoates (II, L=OMe) with guanidine are methanol or THF between 20° C. and the boiling point of these solvents. In most reactions of compounds II with salt-free guanidine, the procedure was advantageously carried out in aprotic inert solvents, such as THF, dimethoxyethane or dioxane. If a base, such as, for example, NaOH is used as solvent, water can also be used in the reaction of II and III.

If L is Cl, the process is carried out advantageously with the addition of an acid scavenger, for example in the form of excess guanidine, to bind the hydrohalic acid.

Some of the basic benzoic acid derivatives of the formula II are known and described in the literature. The unknown compounds of the formula II can be prepared by methods known from the literature.

Carboxylic acids or their esters of the formula II (for example L=—OH or —O-methyl) where R(2) has the meaning of halogen or R(3) has the meaning of nitro can act as useful starting compounds for other carboxylic acids of the formula II, it being possible for the halogen in the position R(2) to be exchanged very conveniently in a known manner for a large number of nucleophilic reagents, such as phenols or alcohols R(4)—C$_n$H$_{2n}$—OH or their alkali metal salts giving the corresponding benzoic acid derivatives. Equally, nitro groups can be reduced to the corresponding aminobenzoic acid by means of Sandmeyer or Ullmann reactions and then lead to the desired, in particular halogen-substituted, benzoic acid derivatives. In many cases, chlorine, bromine or iodine can also be introduced into a particular benzoic acid in a manner known per se by direct halogenation using a Friedel-Crafts catalyst.

In general, benzoylguanidines I are weak bases and can bind acid with the formation of salts. Suitable acid addition salts are salts of all pharmacologically acceptable acids, for example halides, in particular hydrochlorides, lactates, sulfates, citrates, tartrates, acetates, phosphates, methylsulfonates and p-toluenesulfonates.

The compounds I are substituted acylguanidines. The best known representative of the acylguanidines is the pyrazine derivative amiloride, which is used in therapy as a potassium-sparing diuretic. A large number of other compounds of the amiloride type are described in the literature, such as, for example, dimethylamiloride or ethylisopropylamiloride.

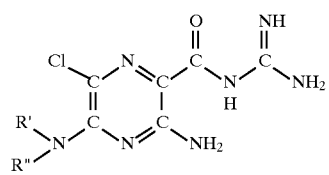

Amiloride: R', R"=H
Dimethylamiloride: R', R"=CH$_3$
Ethylisopropylamiloride: R'=C$_2$H$_5$, R"=CH(CH$_3$)$_2$ Moreover, studies have been published which suggest that amiloride has antiarrhythmic properties (Circulation 79, 1257–63 (1989). However, a broad use as an antiarrhythmic is prevented by the fact that this effect is only weakly pronounced and accompanied by a hypotensive and saluretic activity, and these side effects are undesired in the treatment of cardiac arrhythmias.

Results obtained in experiments with isolated animal hearts have also suggested that amiloride has antiarrhythmic properties (Eur. Heart J. 9 (suppl.1): 167 (1988) (book of abstracts). For example, it has been found on rats' hearts that an artificially induced ventricular fibrillation could be suppressed completely by amiloride. The abovementioned amiloride derivative ethylisopropylamiloride was even more potent than amiloride in this model.

European Offenlegungsschrift 416,499 (HOE 89/F 288) describes benzoylguanidines which have a hydrogen atom in the position which corresponds to the radical R(1).

German Offenlegungsschrift 3,502,629 discloses benzoylguanidines which are substituted in the m-position with a phenoxy group and which always have at least two substituents in the phenoxy group. These compounds are used in crop protection.

The publication Kumamoto, Pharm. Bull [1966], pages 7–13, describes a few substituted benzoylguanidines which can be used as anticancer agents.

U.S. Pat. No. 3,780,027 claims acylguanidines which are similar to the compounds of the formula I with regard to the structure and which are derived from commercially available loop diuretics, such as bumetanide. Accordingly, powerful salidiuretic activity is reported for these compounds.

It was therefore surprising that the compounds according to the invention have no undesired and disadvantageous salidiuretic, but very good antiarrhythmic, properties, such as, for example, in the case of oxygen deficiency symptoms. Due to their pharmacological properties, the compounds are outstandingly suitable for use as antiarrhythmic pharmaceuticals with a cardioprotective component for the prophylaxis and treatment of infarctions and for the treatment of angina pectoris, and they also preventively inhibit, or greatly reduce, the pathophysiological processes involved in ischemically induced damage, in particular when ischemically induced cardiac arrhythmias are triggered. Due to their protective activities against pathological, hypoxic and ischemic situations, the compounds of the formula I according to the invention can be used, due to inhibition of the cellular $Na^+/H^+$ exchange mechanism, as pharmaceuticals for the treatment of all acute or chronic, ischemia-triggered types of damage or diseases which are primarily or secondarily induced thereby. This applies to their use as pharmaceuticals for invasive treatment, for example in the case of organ transplants, where the compounds can be used not only for protecting the organs in the donor before and during removal, for the protection of removed organs, for example when they are treated with, or stored in, physiological bath fluids, but also when they are transferred into the acceptor organism. The compounds are also valuable protective pharmaceuticals for carrying out invasive angioplastic treatment, for example on the heart or on peripheral blood vessels. Due to their protective activity against ischemically induced types of damage, the compounds are also suitable for use as pharmaceuticals for the treatment of ischemias of the nervous system, in particular of the central nervous system, where they are suitable, for example, for the treatment of apoplexy or of cerebral edema. Moreover, the compounds of the formula I according to the invention are also suitable for the treatment of forms of shock, such as, for example, allergic, cardiogenic, hypovolemic and bacterial shock.

Moreover, the compounds of the formula I according to the invention are distinguished by powerful inhibitory action on cell proliferations, for example fibroblast cell proliferation and proliferation of the smooth vascular muscle cells. This is why the compounds of the formula I are suitable as valuable therapeutic agents for diseases in which cell proliferation is a primary or secondary cause, and they can therefore be used as antiatherosclerotics, agents against late complications in diabetes, cancers, fibrotic disorders, such as pulmonary fibrosis, hepatic fibrosis or renal fibrosis, organ hypertrophias and hyperplasias, in particular in prostatic hyperplasia or prostatic hypertrophia.

The compounds according to the invention are valuable inhibitors of the cellular sodium proton antiporter ($Na^+/H^+$ exchanger), which is elevated in a large number of diseases (essential hypertension, atherosclerosis, diabetes and the like) even in those cells which are readily accessible to measurements, such as in erythrocytes, thrombocytes or leukocytes. The compounds according to the invention are therefore suitable as outstanding and simple scientific tools, for example in their use as diagnostics for determining, and distinguishing between certain forms of hypertension, but also of atherosclerosis, diabetes, proliferative diseases, and the like. Moreover, the compounds of formula I are suitable for preventive therapy for preventing the genesis of hypertension, such as of essential hypertension.

Moreover, the compounds are distinguished by an inhibition of the hydrochloric acid production of the parietal cells of the stomach, and they can therefore be used as pharmaceuticals for the treatment of gastrointestinal diseases. Such gastrointestinal disorders and diseases of the esophagus are, for example, gastric and intestinal ulcers and reflux esophagitis.

Pharmaceuticals which contain a compound I can be administered orally, parenterally, intravenously, rectally or by inhaling, the preferred way of administration being dependent on the particular symptom of the disease. The compounds I can be used by themselves or together with pharmaceutical auxiliaries, and they can be employed both in veterinary medicine and human medicine.

A person skilled in the art knows, on the basis of his expert knowledge, which auxiliaries are suitable for the desired pharmaceutical formulation. Auxiliaries which can be used in addition to solvents, gel-formers, bases for suppositories, tableting auxiliaries, and other excipients for active substances are, for example, antioxidants, dispersants, emulsifiers, antifoamers, flavor improvers, preservatives, solubilizers or colorants.

For an oral dosage form, the active compounds together with the additives suitable for this purpose, such as carriers, stabilizers or inert diluents, are mixed and formulated by customary methods to give suitable dosage forms, such as tablets, sugar-coated tablets, hard gelatin capsules, or aqueous, alcoholic or oily solutions. Inert excipients which may be used are, for example, gum arabic, magnesia, magnesium carbonate, potassium phosphate, lactose, glucose or starch, in particular maize starch. Dry granules or moist granules can be used for the preparation. Examples of oily excipients or examples of solvents are vegetable or animal oils, such as sunflower oil or codliver oil.

For subcutaneous or intravenous administration, the active compounds, if desired together with the substances which are customary for this purpose, such as solubilizers, emulsifiers or other auxiliaries, are dissolved, suspended or emulsified. Examples of suitable solvents are: water, physiological saline, or alcohols, for example ethanol, propanol, glycerol, and also sugar solutions, such as glucose or mannitol solutions, or else a mixture of the various solvents which have been mentioned above.

Pharmaceutical formulations which are suitable for administration in the form of aerosols or sprays are, for example, solutions, suspensions or emulsions of the active substance of the formula I in a pharmaceutically acceptable solvent, such as, in particular, ethanol or water, or else in a mixture of such solvents.

If required, the formulation can also contain other pharmaceutical auxiliaries, such as surfactants, emulsifiers and stabilizers, and a propellant gas. The concentration of active substances in such a preparation is generally from about 0.1 to 10, in particular from about 0.3 to 3, % by weight.

The dose of the active substance of the formula I to be administered and the frequency of the administration will depend on the potency and duration of action of the compounds used; in addition also on the nature and severity of the disease to be treated and on the sex, age, weight and individual responsiveness of the mammal to be treated.

On average, the daily dosage rate of a compound of the formula I in the case of a patient of approximately 75 kg will be at least 0.001 mg/kg, preferably 0.01 mg/kg, up to not more than 10 mg/kg, preferably 1 mg/kg, of body weight. If the disease is acute, such as immediately after suffering a cardiac infarction, even higher, and in particular, more frequent, doses may also be required, for example up to 4 single doses per day. Up to 200 mg per day may be required, in particular for intravenous administration, such as in the case of a patient who has suffered an infarction and is under intensive care.

EXPERIMENTAL PART

General Protocol for the Preparation of Benzoylguanidines (I) from Benzoic Acids (II, L=OH)

0.01 mol of the benzoic acid derivative of the formula II is dissolved or suspended in 60 ml of anhydrous tetrahydrofuran (THF), and 1.78 g (0.011 mol) of carbonyldiimidazole are then added. After the reaction solution has been stirred for 2 hours at room temperature, 2.95 g (0.05 mol) of guanidine are introduced. After the mixture has been stirred overnight, the THF is distilled off under reduced pressure (Rotavapor), water is added, the pH is brought to 6–7 using 2N HCl, and the corresponding benzoylguanidine (formula I) is filtered off. The resulting benzoylguanidines can be converted to the corresponding salts by being treated with aqueous or methanolic hydrochloric acid or other pharmacologically tolerated acids.

EXAMPLE 1

3,5-Dichlorobenzoylguanidine hydrochloride from 3,5-dichlorobenzoic acid following the general protocol; colorless crystals, m.p. 286° C.

EXAMPLE 2

3-Chlorobenzoylguanidine hydrochloride from 3-chlorobenzoic acid following the general protocol; colorless crystals, m.p. 175° C.

EXAMPLE 3

3,4-Dimethylbenzoylguanidine hydrochloride from 3,4-dimethylbenzoic acid following the general protocol; colorless crystals, m.p. 276° C.

EXAMPLE 4

3-Trifluoromethylbenzoylguanidine hydrochloride from 3-trifluoromethylbenzoic acid following the general protocol; colorless crystals, m.p. 170° C.

EXAMPLE 5

3,5-Dichloro-4-hydroxybenzoylguanidine hydrochloride from 3,5-dichloro-4-hydroxybenzoic acid following the general protocol; colorless crystals, m.p. 254°–256° C.

EXAMPLE 6

3,5-Di-tert-butyl-4-hydroxybenzoylguanidine hydrochloride from 3,5-di-tert-butyl-4-hydroxybenzoic acid following the general protocol; colorless crystals, m.p. 163°–165° C.

EXAMPLE 7

3,5-Difluorobenzoylguanidine hydrochloride from 3,5-difluorobenzoic acid following the general protocol; colorless crystals, m.p. 224° C.

EXAMPLE 8

4-Trifluoromethylbenzoylguanidine hydrochloride from 4-trifluoromethylbenzoic acid following the general protocol; colorless crystals, m.p. 215° C.

EXAMPLE 9

3-Chloro-5-trifluoromethylbenzoylguanidine hydrochloride from 3-chloro-5-trifluoromethylbenzoic acid following the general protocol; colorless crystals, m.p. 162° C.

EXAMPLE 10

3,5-Bistrifluoromethylbenzoylguanidine hydrochloride from 3,5-bistrifluoromethylbenzoic acid following the general protocol; colorless crystals, m.p. 214° C.

EXAMPLE 11

5-Trifluoromethyl-3-iodobenzoylguanidine hydrochloride from 5-trifluoromethyl-3-iodobenzoic acid following the general protocol; colorless crystals, m.p. 263° C.

EXAMPLE 12

3,5-Dimethylbenzoylguanidine hydrochloride from 3,5-dimethylbenzoic acid following the general protocol; colorless crystals, m.p. 216°–219° C.

EXAMPLE 13

4-tert-Butylbenzoylguanidine hydrochloride from 4-tert-butylbenzoic acid following the general protocol; colorless crystals, m.p. 237°–240° C.

EXAMPLE 14

4-Chloro-3-methylbenzoylguanidine hydrochloride from 4-chloro-3-methylbenzoic acid following the general protocol; colorless crystals, m.p. 249°–251° C.

EXAMPLE 15

3,5-Dichloro-4-(4-chlorobenzyloxy)benzoylguanidine hydrochloride from 3,5-dichloro-4-(4-chlorobenzyloxy) benzoic acid following the general protocol; colorless crystals, m.p. 230°–231° C.

3,5-Dichloro-4-(4-chlorobenzyloxy)benzoic acid was obtained by reacting 3,5-dichloro-4-hydroxybenzoic acid with 4-chlorobenzyl chloride in DMF in the presence of potassium carbonate at 40° C., followed by hydrolysis of the 4-chlorobenzyl 3,5-dichloro-4-(4-chlorobenzyloxy) benzoate in aqueous/methanolic solution with NaOH and subsequent acidification using 2N HCl, m.p. 215°–220° C.

EXAMPLE 16

4-tert-Butylbenzoylguanidine is obtained by treating the corresponding hydrochloride of Example 19 with triethylamine in dimethylformamide and water. Colorless, crystalline substance, m.p. 255°–258° C.

EXAMPLE 17

3,5-Dibromobenzoylguanidine hydrochloride is obtained from 3,5-dibromobenzoylguanidine (Example 28) by treatment with methanolic hydrochloric acid. Colorless crystals, m.p. 275° C.

EXAMPLE 18

3-Azido-5-trifluoromethylbenzoylguanidine hydrochloride is obtained from 3-azido-5-trifluoromethylbenzoic acid following the general protocol (m.p. 123°–125° C.), which is prepared from 3-amino-5-trifluoromethylbenzoic acid and sodium azide by diazotization and then by Sandmeyer reaction. Colorless, crystalline compound. m.p. 197° C.

EXAMPLE 19

4-Bromo-3-methylbenzoylguanidine hydrochloride is obtained from 4-bromo-3-methylbenzoic acid following the general protocol. Colorless crystals. m.p. 250° C.

EXAMPLE 20

3-Chloro-4-fluorobenzoylguanidine hydrochloride is obtained from 3-chloro-4-fluorobenzoic acid following the general protocol. Colorless crystals. m.p. 188°–189° C.

EXAMPLE 21

3,5-Di-tert-butylbenzoylguanidine hydrochloride is obtained from 3,5-di-tert-butylbenzoic acid following the general protocol. Colorless crystals. m.p. 180° C.

EXAMPLE 22

3-Bromo-5-chlorobenzoylguanidine hydrochloride is obtained from 3-bromo-5-chlorobenzoic acid following the general protocol. Colorless crystals. m.p. 268° C.

EXAMPLE 23

4-Bromo-3-trifluoromethylbenzoylguanidine hydrochloride

Colorless crystals, m.p. 211° C.

Synthesis route:

a) 4-Bromo-3-trifluoromethylbenzonitrile from 4-bromo-3-trifluoromethylaniline under Sandmeyer conditions: diazotization of the amine using sodium nitrite in half-concentrated sulfuric acid at 0° C. followed by reaction with Cu(I)CN (from copper sulfate, sodium sulfite and NaCN), first at 0° C. then slowly heating at room temperature. Aqueous work-up is followed by column chromatography using ethyl acetate/n-heptane 2:8, colorless crystals, m.p. 77°–80° C.

b) 4-Bromo-3-trifluoromethylbenzoic acid from a) by acid catalyzed hydration by means of glacial acetic acid/concentrated sulfuric acid under reflux for 4 hours, aqueous work-up, colorless crystals, m.p. 177°–80° C.

c) 4-Bromo-3-trifluoromethylbenzoylguanidine hydrochloride from b) following the general protocol

EXAMPLE 24

4-Isopropyl-3-trifluoromethylbenzoylguanidine hydrochloride

Colorless crystals, m.p. 213°–14° C.

Synthesis route:

a) Methyl 4-bromo-3-trifluoromethylbenzoate from 4-bromo-3-trifluoromethylbenzoic acid (23b) by heating in methanol in the presence of acetyl chloride, aqueous work-up, colorless crystals, m.p. 56°–57° C.

b) Methyl 4-isopropyl-3-trifluoromethylbenzoate from methyl 4-bromo-3-trifluoromethylbenzoate (a) by cross-coupling using 1.5 equivalents of isopropyl-zinc chloride (obtained from isopropylmagnesium chloride by transmetallation using zinc(II) chloride etherate in THF) by stirring at room temperature in the presence of catalytic amounts of palladium(II) [1,1'-bis(diphenylphosphino)-ferrocene] chloride and copper(I) iodide, aqueous work-up, extraction using ethyl acetate, followed by column chromatography on silica gel using ethyl acetate/cyclohexane (2:8), colorless oil.

c) 4-Isopropyl-3-trifluoromethylbenzoylguanidine hydrochloride by heating to the boil in THF in the presence of guanidine followed by hydrochloride formation

EXAMPLE 25

4-Cyclopentyl-3-trifluoromethylbenzoylguanidine hydrochloride

Colorless crystals, m.p. 229°–31° C.

Synthesis route:

a) Methyl 4-cyclopentyl-3-trifluoromethylbenzoate from methyl 4-bromo-3-trifluoromethylbenzoate (24a) by cross-coupling with cyclopentylzinc chloride analogously to Example 24b), colorless oil b) 4-Cyclopentyl-3-trifluoromethylbenzoylguanidine hydrochloride analogously to 24c).

EXAMPLE 26

3-Methyl-5-trifluoromethylbenzoylguanidine hydrochloride

Colorless crystals, m.p. 181°–82° C.

Synthesis route:

a) Methyl 3-iodo-5-trifluoromethylbenzoate from 3-iodo-5-trifluoromethylbenzoic acid analogously to Example 24a), colorless oil b) Methyl 3-methyl-5-trifluoromethylbenzoate from methyl 3-iodo-5-trifluoromethylbenzoate by cross-coupling using methylzinc chloride analogously to Example 24b), colorless oil b) 3-Methyl-5-trifluoromethylbenzoylguanidine hydrochloride analogously to 24c)

EXAMPLE 27

3-Isopropyl-5-trifluoromethylbenzoylguanidine hydrochloride

Colorless crystals, m.p. 110°–12° C.

Synthesis route:

a) Methyl 3-isopropyl-5-trifluoromethylbenzoate from methyl 3-iodo-5-trifluoromethylbenzoate (26a) by cross-coupling with isopropylzinc chloride analogously to 24b), colorless oil b) 3-Isopropyl-5-trifluoromethylbenzoylguanidine hydrochloride analogously to 24c)

EXAMPLE 28

3-Cyclopentyl-5-trifluoromethylbenzoylguanidine hydrochloride

Colorless crystals, m.p. 110° C. with decomposition

Synthesis route:

a) Methyl 3-cyclopentyl-5-trifluoromethylbenzoate from methyl 3-iodo-5-trifluoromethylbenzoate (26a) (by cross-coupling with cyclopentylzinc chloride analogously to 24b), colorless oil b) 3-Cyclopentyl-5-trifluoromethylbenzoylguanidine hydrochloride analogously to 24c)

EXAMPLE 29

3-Phenyl-5-trifluoromethylbenzoylguanidine hydrochloride

Colorless crystals, m.p. 217°–21° C.

Synthesis route:

a) Methyl 3-phenyl-5-trifluoromethylbenzoate from methyl 3-iodo-5-trifluoromethylbenzoate (26a) by cross-coupling with 1.1 equivalents of phenylboronic acid in aqueous methanol/toluene mixture (reflux, 4 hours) in the presence of catalytic amounts of palladium acetate, triphenylphosphine and sodium carbonate, distill off the solvent, take up the residue in ethyl acetate, render the mixture neutral using dilute hydrochloric acid and, after aqueous work-up, subject to column chromatography on silica gel using ethyl acetate/cyclohexane (3:7), colorless oil b) 3-Phenyl-5-trifluoromethylbenzoylguanidine hydrochloride analogously to 24c)

EXAMPLE 30

4-Fluoro-3-trifluoromethylbenzoylguanidine hydrochloride

Colorless crystals, m.p. 159°–60° C. from 4-fluoro-3-trifluoromethylbenzoic acid following the general protocol

EXAMPLE 31

4-Phenoxy-3-trifluoromethylbenzoylguanidine hydrochloride

Colorless crystals, m.p. 162°–65° C. from 4-fluoro-3-trifluoromethylbenzoylguanidine (30 base) by reaction with phenol in the presence of potassium carbonate in DMF at 120° C., aqueous work-up, column chromatography, methylene chloride/methanol 9:1, followed by hydrochloride formation

EXAMPLE 32

4-(4-Fluorophenoxy)-3-trifluoromethylbenzoylguanidine hydrochloride

Colorless crystals, m.p. 165°–67° C. from (30 base) analogously to process (31) by means of 4-fluorophenol

EXAMPLE 33

4-(4-Chlorophenoxy)-3-trifluoromethylbenzoylguanidine hydrochloride

Colorless crystals, m.p. 195°–97° C. from (30 base) analogously to process (31) by means of 4-chlorophenol

EXAMPLE 34

5-Fluoro-3-trifluoromethylbenzoylguanidine hydrochloride

Colorless crystals, m.p. 150°–51° C. from 5-fluoro-3-trifluoromethylbenzoic acid following the general protocol

EXAMPLE 35

4-Phenylethynyl-3-trifluoromethylbenzoylguanidine hydrochloride

Colorless crystals, m.p. 150° C. with decomposition

Synthesis route:

a) Methyl 4-phenylethynyl-3-trifluoromethylbenzoate from methyl 4-bromo-3-trifluoromethylbenzoate (24a) by Stephans-Castro coupling with 2.5 equivalents of phenylacetylene, stirring at room temperature for 24 hours in the presence of catalytic amounts (5 mol %) of bis(triphenylphosphine)palladium(II) chloride, 15 mol % of copper(I) iodide and 3 equivalents of n-butylamine, work-up with aqueous ammonium chloride, extraction with ethyl acetate followed by column chromatography on silica gel using ethyl acetate/cyclohexane (3:7), pale brownish oil.

b) 4-Phenylethynyl-3-trifluoromethylbenzoylguanidine hydrochloride analogously to 24c)

EXAMPLE 36

3-Bromo-4-methylbenzoylguanidine hydrochloride is obtained from 3-bromo-4-methylbenzoic acid analogously to the general protocol. Colorless crystals. m.p. 250° C.

EXAMPLE 37

3-Chloro-4-isopropylbenzoylguanidine hydrochloride is obtained from 3-chloro-4-isopropylbenzoic acid analogously to the general protocol. Colorless crystals. m.p. 185° C.

EXAMPLE 38

3,4,5-Trichlorobenzoylguanidine hydrochloride is obtained from 3,4,5-trichlorobenzoic acid analogously to the general protocol. Colorless crystals. m.p. 194° C.

EXAMPLE 39

3-Bromo-5-methylbenzoylguanidine hydrochloride is obtained from 3-bromo-5-methylbenzoic acid analogously to the general protocol. Colorless crystals. m.p. 235°–236° C.

EXAMPLE 40

4-Chloro-3,5-dimethylbenzoylguanidine hydrochloride is obtained from 4-chloro-3,5-dimethylbenzoic acid analogously to the general protocol. Colorless crystals. m.p. 244°–247° C.

EXAMPLE 41

3-Trifluoromethyloxybenzoylguanidine hydrochloride is obtained from 3-trifluoromethyloxybenzoic acid analogously to the general protocol. Crystals. m.p. 146°–148° C.

EXAMPLE 42

4-Trifluoromethyloxybenzoylguanidine hydrochloride is obtained from 4-trifluoromethyloxybenzoic acid analogously to the general protocol. Crystals. m.p. 259° C.

EXAMPLE 43

4-Cyclohexylbenzoylguanidine hydrochloride is obtained from 4-cyclohexylbenzoic acid analogously to the general protocol. Crystals. m.p. 273° C.

EXAMPLE 44

3-Chloro-4-cyclopentyloxybenzoylguanidine hydrochloride is obtained from 3-chloro-4-cyclopentyloxybenzoic acid analogously to the general protocol. Colorless crystals. m.p. 273° C.

3-Chloro-4-cyclopentyloxybenzoic acid, of m.p. 148°–151° C., is obtained by hydrolysis of methyl 3-chloro-4-cyclopentyloxybenzoate (amorphous oily substance) in a mixture of aqueous NaOH and dioxane followed by acidification of the alkaline hydrolysis solution using half-concentrated hydrochloric acid.

Methyl 3-chloro-4-cyclopentyloxybenzoate is obtained by boiling methyl 3-chloro-4-hydroxybenzoate and iodocyclopentane in acetone in the presence an excess of solid, ground potassium carbonate. After the acetone has been evaporated, the oily residue is taken up in water, the mixture is subsequently extracted using ethyl acetate, the extract is dried over sodium sulfate, and the solvent is then evaporated.

EXAMPLE 45

3-Isopropyl-4-methoxybenzoylguanidine hydrochloride is obtained from 3-isopropyl-4-methoxybenzoic acid analogously to the general protocol. Colorless crystals. m.p. 214° C.

EXAMPLE 46

3-Chloro-4-cyclooctyloxybenzoylguanidine hydrochloride is obtained from 3-chloro-4-cyclooctyloxybenzoic acid analogously to the general protocol. Colorless crystals. m.p. 243° C.

3-Chloro-4-cyclooctyloxybenzoic acid, of m.p. 110°–112° C., is obtained by hydrolysis of methyl 3-chloro-4-cyclooctyloxybenzoate (amorphous oily substance) in a mixture of aqueous NaOH and methanol, followed by acidification of the alkaline hydrolysis solution with half-concentrated hydrochloric acid.

Methyl 3-chloro-4-cyclooctyloxybenzoate is obtained by heating methyl 3-chloro-4-hydroxybenzoate and cyclooctyl bromide in dimethylformamide for 20 hours in the presence of an excess of solid, ground potassium carbonate. After the solvent has been evaporated, the oily residue is taken up in water, the mixture is subsequently extracted using ethyl acetate, the extract is dried over sodium sulfate, and the solvent is then evaporated.

EXAMPLE 47

4-tert-Butyl-3-methoxybenzoylguanidine hydrochloride is obtained from 4-tert-butyl-3-methoxybenzoic acid analogously to the general protocol. Colorless crystals. m.p. 227°–231° C.

The 4-tert-Butyl-3-methoxybenzoic acid used is obtained by oxidation of 4-tert-butyl-3-methoxytoluene in an aqueous/alkaline solution of potassium permanganate.

EXAMPLE 48

3-Bromo-4-fluorobenzoylguanidine hydrochloride is obtained from 3-bromo-4-fluorobenzoic acid analogously to the general protocol. Colorless crystals. m.p. 215° C.

EXAMPLE 49

3-tert-Butyl-4-hydroxybenzoylguanidine hydrochloride is obtained from 3-tert-butyl-4-hydroxybenzoic acid analogously to the general protocol. Colorless crystals. m.p. 216° C.

EXAMPLE 50

3-Cyano-4-methoxybenzoylguanidine hydrochloride is obtained from 3-cyano-4-methoxybenzoic acid analogously to the general protocol. Colorless crystals. m.p. 236° C.

EXAMPLE 51

3-tert-Butyl-4-methoxybenzoylguanidine hydrochloride is obtained from 3-tert-butyl-4-methoxybenzoic acid analogously to the general protocol. Colorless crystals. m.p. 260°–62° C.

EXAMPLE 52

3-Chloro-4-(1-hexyl)benzoylguanidine hydrochloride is obtained from 3-chloro-4-(1-hexyl)benzoic acid analogously to the general protocol. Colorless crystals. m.p. 286° C. (decomposition).

EXAMPLE 53

3-tert-Butyl-4-(2-methyl-1-propyl)benzoylguanidine hydrochloride is obtained from 3-tert-butyl-4-(2-methyl-1-propyl)benzoic acid analogously to the general protocol. Colorless crystals.
m.p. 218°–228° C. (decomposition).

EXAMPLE 54

4-Isopropyl-3-pentafluoroethylbenzoylguanidine hydrochloride is obtained from 4-isopropyl-3-pentafluoroethylbenzoic acid analogously to the general protocol. Colorless, amorphous solid.

EXAMPLE 55

3-tert-Butyl-4-isopropylbenzoylguanidine hydrochloride is obtained from 3-tert-butyl-4-isopropylbenzoic acid analogously to the general protocol. Colorless crystals. m.p. 145°–165° C.

EXAMPLE 56

4-Isopropylbenzoylguanidine hydrochloride is obtained from isopropylbenzoic acid analogously to the general protocol. Colorless crystals. m.p. 193°–198° C.

EXAMPLE 57

3-Trifluoromethylbenzoylguanidine is obtained from 3-trifluorobenzoic acid analogously to the general protocol. Colorless, amorphous-oily composition.

EXAMPLE 58

3-Trifluoromethylbenzoylguanidine methanesulfonate is obtained analogously to the general protocol from 3-trifluoromethylbenzoylguanidine by treating the latter with methanesulfonic acid in ethyl acetate. Colorless crystals. m.p. 167°–170° C.

EXAMPLE 59

4-Fluoro-3-isobutylbenzoylguanidine hydrochloride is obtained from 4-fluoro-3-isobutylbenzoylguanidine analogously to the general protocol. m.p. 136°–140° C.

We claim:
1. A benzoylguanidine of the formula I

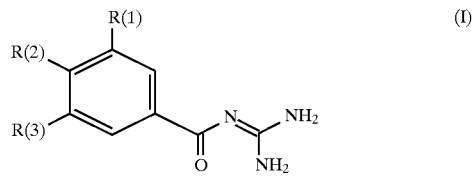

in which:
one of the substituents R(1), R(2) and R(3) is $N_3$, CN, OH or $(C_1-C_{10})$-alkyloxy, if at least one of the remaining substituents R(1), R(2) or (R3) is an alkyl radical having 3 to 12 carbon atoms, or
one of the substituents R(1), R(2) or R(3) is
R(4)—$C_nH_{2n}$—$O_m$ where
m is zero or 1,
n is zero, 1, 2 or 3,
R(4) is $C_pF_{2p+1}$
where p is 1, 2 or 3 if n is zero or 1, or
R(4) is $(C_3-C_{12})$-cycloalkyl, phenyl, or phenyl substituted by a substituent selected from the group consisting of F, Cl, $CF_3$, methyl, methoxy or NR(5)R(6), where R(5) and R(6) are hydrogen and $(C_1-C_4)$-alkyl, or
one of the substituents R(1), R(2) or R(3) is —C≡CR(5), —C=CR(5),
R(5) is phenyl
which is unsubstituted or substituted by 1–3 substituents selected from the group consisting of F, Cl, $CF_3$, methyl, methoxy, hydroxyl, amino, methylamino and dimethylamino, or
R(5) is $(C_1-C_6)$-alkyl,
which is unsubstituted or substituted by 1–3 OH, or
R(5) is $(C_3-C_8)$-cycloalkyl,
R(6) is hydrogen or methyl,
or R(1), R(2), and R(3) are hydrogen, F, Cl, Br, I, or $(C_1-C_{12})$ alkyl;
and the pharmacologically acceptable salts thereof, with the exception of the compounds benzoylguanidine, 4-chlorobenzoylguanidine, 3,4-dichlorobenzoylguanidine and 3- or 4-methylbenzoylguanidine.
2. A benzoylguanidine of the formula I as claimed in claim 1, in which:
one of the substituents R(1), R(2) or R(3) is OH or $(C_1-C_6)$-alkyloxy, if at least one of the remaining substituents R(1), R(2) and R(3) is an alkyl radical having 3 to 6 carbon atoms, or one of the substituents R(1), R(2) or R(3) is
R(4)—$C_n$—$H_{2n}O_m$ where
m is zero or 1,
n is zero, 1, 2 or 3,
R(4) is $C_pF_{2p+1}$
where p is 1 if n is zero or 1, or
R(4) is ($C_5$–$C_7$)-cycloalkyl, phenyl, or phenyl substituted by a substituent selected from the group conssiting of F, Cl, $CF_3$, methyl and methoxy, or
one of the substituents R(1), R(2) or R(3) is —C≡CR(5),
R(5) is phenyl or ($C_1$–$C_4$)-alkyl,
which is unsubstituted or substituted by an OH,
and the remaining R(1), R(2) and R(3) substituents are F, Cl, Br, or ($C_1$–$C_8$)-alkyl;
and the pharmacologically acceptable salts thereof.

3. A pharmaceutical composition comprising a pharmaceutically acceptable carrier and a pharmaceutically acceptable amount of a compound I as claimed in claim 1.

4. A benzoylguanidine of the formula I as claimed in claim 1, selected from the group comprising 3-trifluoromethylbenzoylguanidine hydrochloride, 3,5-bistrifluoromethylbenzoylguanidine hydrochloride, 3-methyl-5-trifluoromethylbenzoylguanidine hydrochloride, 4-fluoro-3-trifluoromethylbenzoylguanidine hydrochloride, 4-(4-fluorophenoxy)-3-trifluoromethylbenzoylguanidine hydrochloride, 5-fluoro-3-trifluoromethylbenzoylguanidine hydrochloride, 3-chloro-4-isopropylbenzoylguanidine hydrochloride, 4-tert-butyl-3-methoxybenzoylguanidine hydrochloride, 3-tert-butyl-4-hydroxybenzoylguanidine hydrochloride and 3-tert-butyl-4-isopropylbenzoylguanidine hydrochloride.

5. A method for the treatment of arrhythmias, which comprises administering to a host in need of said treatment an effective amount of a compound of the formula I as claimed in claim 1.

6. A method for the treatment or prophylaxis of ischemic heart conditions which comprises administering to a host an effective amount of a compound of the Formula I as claimed in claim 1.

* * * * *

UNITED STATES PATENT AND TRADEMARK OFFICE
CERTIFICATE OF CORRECTION

PATENT NO.   : 5,866,610
DATED        : February 2, 1999
INVENTOR(S)  : Lang et al.

It is certified that error appears in the above-identified patent and that said Letters Patent is hereby corrected as shown below:

Column 15,
Line 9, "ssiting" should read -- sisting --.
Line 13, "and the remaining" should read -- or -- and "substituents are" should read -- are hydrogen, --.

Signed and Sealed this

Twenty-first Day of January, 2003

JAMES E. ROGAN
*Director of the United States Patent and Trademark Office*